United States Patent [19]

Scarffe

[11] Patent Number: 5,460,522

[45] Date of Patent: Oct. 24, 1995

[54] SLIDABLE ASSEMBLIES AND PROBE ELEMENTS

[75] Inventor: Michael F. Scarffe, Milton Keynes, England

[73] Assignee: Aztec Developments Limited, Milton Keynes, England

[21] Appl. No.: 174,311

[22] Filed: Dec. 30, 1993

[30] Foreign Application Priority Data

Jun. 16, 1993 [GB] United Kingdom ............ 9312401

[51] Int. Cl.⁶ .................................................. A61C 19/04
[52] U.S. Cl. .................. 433/72; 128/776; 33/514
[58] Field of Search ............ 433/72, 75; 128/776; 33/513, 514; 600/40

[56] References Cited

U.S. PATENT DOCUMENTS

| | | | |
|---|---|---|---|
| 4,666,426 | 5/1987 | Mattioli et al. | 600/40 |
| 4,677,756 | 7/1987 | Simon et al. | 33/514 |
| 4,764,114 | 8/1988 | Jeffcoat et al. | 433/72 |
| 4,836,780 | 6/1989 | Buchanan | 433/102 |
| 4,960,132 | 10/1990 | Habekost | 433/72 |
| 4,979,898 | 12/1990 | Rand | 33/513 |
| 5,044,951 | 9/1991 | Sheridan | 433/72 |
| 5,178,537 | 1/1993 | Currie | 433/72 |

FOREIGN PATENT DOCUMENTS

| | | | |
|---|---|---|---|
| 119813 | 9/1984 | European Pat. Off. . | |
| 0248455 | 12/1987 | European Pat. Off. . | |
| 0296520 | 12/1988 | European Pat. Off. | 128/776 |
| WO9003162 | 4/1990 | European Pat. Off. . | |
| WO9011046 | 10/1990 | European Pat. Off. . | |
| WO9116854 | 11/1991 | European Pat. Off. . | |
| 2662599 | 12/1991 | France | 433/72 |
| 0422916 | 1/1935 | United Kingdom . | |
| 2086232 | 5/1982 | United Kingdom . | |
| 2178505 | 2/1986 | United Kingdom . | |
| 2193579 | 9/1986 | United Kingdom . | |

*Primary Examiner*—Cary E. O'Connor
*Attorney, Agent, or Firm*—Cushman, Darby & Cushman

[57] ABSTRACT

A probe element for probe apparatus such as a dental probe comprises a curved tubular sheath having a proximal end for connection to main body of the probe apparatus and on open distal end. A probe member slides within the sheath and has a proximal end for connection to position sensing components in the probe apparatus main body and a distal end that protrudes by a variable extent from the open distal end of the sheath. Within the sheath the probe member is made up of a series of relatively large diameter beads joined by smaller diameter bridges to provide improved mobility of the probe member in the sheath even after prolonged storage.

10 Claims, 1 Drawing Sheet

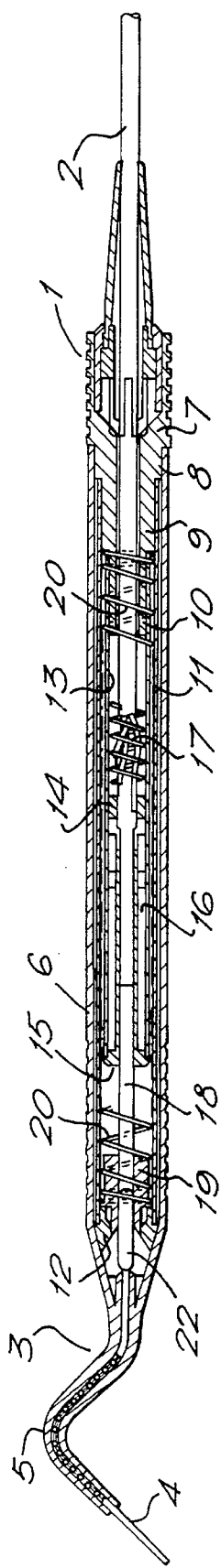
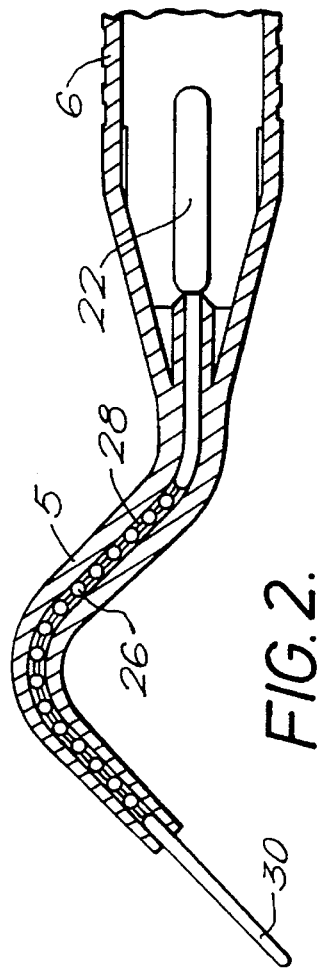
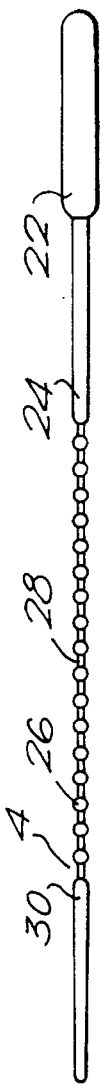
FIG.1.
FIG.2.
FIG.3.

SLIDABLE ASSEMBLIES AND PROBE ELEMENTS

The present invention relates to slidable assemblies comprising an elongate core slidable within a tubular sheath and has particular relevance to probe elements for probe apparatus in which said elongate core constitutes a probe member protruding from said sheath by a variable extent.

GB-B-2193579 describes a measuring instrument particularly for use in measuring the depth of periodontal pockets which has a probe member sliding within a tubular sheath and protruding therefrom by a variable extent at its distal end. The proximal end of the tubular sheath is connected to the housing member of the measuring instrument and the proximal end of the probe member is connected to sensing means within the housing member to enable the production of an electrical signal indicative of the degree of protrusion of the distal tip of the probe member from the sheath. For the successful operation of the apparatus described it is necessary that the probe member slide within the sheath freely. Typically, the probe member is a plastics fiber of small diameter which is a close sliding fit within the tubular bore of the sheath. In order to provide adequate access by a dental surgeon to a periodontal pocket, the sheath will generally be curved in a "swan-neck" shape. The probe member is sufficiently flexible to slide within the curved sheath with acceptably low friction despite the need for the probe member to flex as it slides in the "swan-neck" portion of the sheath.

It has now been surprisingly discovered that whilst a freshly inserted probe member may slide with acceptable friction within the sheath, on storage without sliding movement, the plastics probe member may take on a set to the shape of the curve of the tubular sheath and thereafter the frictional force involved in sliding the probe member in the sheath is found to be increased by virtue of the resistance of the set curve of the probe member to flexing to follow the curve of the sheath as the probe member slides.

More generally, there are many situations in which it is desirable to provide an elongate core sliding within a curved tubular sheath and flexing to follow the curve thereof with relatively low resistance, when a solid core of a diameter approaching that of the bore of the sheath would be too stiff.

The present invention accordingly provides in a first aspect a slidable assembly comprising a curved tubular sheath containing an elongate core slidable within the sheath, wherein said core comprises over at least a part of its length within said sheath a series of larger cross-section portions linked by smaller cross-section flexible bridges.

In a second aspect, the invention provides a probe element for probe apparatus which element comprises a curved tubular sheath having a proximal end for connection to the probe apparatus and an open distal end, and a probe member within said sheath having a proximal end for connection to the probe apparatus and a distal end for protrusion from said distal end of the sheath, said sheath and probe member being slidable with respect to one another to protrude said distal end of the probe member from the distal end of the sheath by a variable amount, wherein said probe member comprises over at least a portion of its length within said sheath a series of larger cross-section portions linked by smaller cross-section flexible bridges.

The larger cross-section portions are preferably a close sliding fit within the bore of the tubular sheath.

Preferably, the larger cross-section portions may have a length to breadth ratio in the range of 0.5:1 to 3:1, more preferably substantially 1:1.

The ratio of the length of the bridges to the length of the larger cross-section portions is also preferably about 1:1 but generally may be selected within the range of 0.5:1 to 10:1.

The breadth of the larger cross-section portions in said probe member is preferably from 0.2 to 1 mm, e.g. about 0.5 mm.

The breadth of the bridges is preferably from 0.05 to 0.5 mm, preferably about 0.2 mm, but always such that the cross-sectional area of the bridges is less than that of the larger cross-section portions so as to reduce the tendency of the probe member to accept a set.

Preferably, the distal end of the probe primer comprises a terminal portion of substantially uniform or progressively or stepwise tapering cross-section which is substantially stiffer than said part of the length of the probe member comprising said flexible bridges.

Preferably, at least a proximal part of said terminal portion is at least substantially straight. Preferably also the distal end portion of the sheath is substantially straight.

Preferably, all of that part of the probe member which lies within a curved part of the sheath comprises said larger cross-section portions and linking bridges.

Preferably, the proximal end of the probe member comprises a relatively stiff terminal portion of enlarged breath for connection to said probe apparatus.

Preferably, the larger cross-section portions of said probe member and said bridges are integrally connected. For instance the probe member may be moulded in plastics material.

The invention includes in a third aspect probe apparatus, e.g. apparatus for measuring the depth of a cavity, comprising a housing member, a probe element of the kind described above according to the invention, one of said probe member and said sheath being connected at its proximal end to said housing member, slidable means disposed in said housing for sliding movement therein and coupled to the other of said probe member and said sheath to slide therewith, and means for sensing the position of said slidable means in said housing member and for producing a signal indicative thereof and of the extent of protrusion of said distal end of said probe member from said sheath.

Preferably, said probe apparatus is substantially as described in GB-B-2193579 but incorporating a probe element according to this invention.

The invention will be further described and illustrated with the reference to the accompanying drawings in which:

FIG. 1 is a cross-sectional view of probe apparatus according to the third aspect of the invention;

FIG. 2 is a longitudinal cross-section through a probe element according to the second aspect of the invention; and FIG. 3 is a side view of a probe member for use in the probe element of FIG. 2.

The measuring instrument illustrated in FIG. 1 comprises a hand piece 1 connected via a cable 2 to a computer and printer installation (not shown). The hand piece 1 comprises a disposable portion and non-disposable portion. The disposable portion comprises a probe element 3 comprising a probe member 4 slidable within a sheath 5. The sheath 5 is formed integrally with a cylindrical cover member 6 which is open at one end and leads into the sheath 5 at the other end. The sheath 5 and the probe member 4 are shown in detail in FIGS. 2 and 3 and are further described hereafter. It should be noted however that the probe member 4 is a free-sliding fit in the sheath 5.

The non-disposable portion comprises a plastics hollow rear plug member 7 having a bore through which passes the cable 2 and having first, second and third reduced diameter portions 8, 9 and 10, reducing stepwise in diameter toward the front of the probe. Over the first reduced diameter portion 8 the open end of the plastics cover member 6 is received as a push-fit. Over the second reduced diameter portion 9 there is received as a tight push-fit a stainless steel tubular member 11. At its opposite end, tubular member 11 receives an annular plastics nose member 12 which wedges into the conical transition between the cover member 6 and the sheath 5.

Over the third reduced diameter portion 10 of the rear plug member 7 there is received a second stainless steel tubular member 13 so that a small annular gap is formed between stainless steel tubular members 11 and 13. Pushed into the forward end of the second stainless steel tubular member 13 is a plastics bobbin 14 having a hollow cylindrical body portion and enlarged cylindrical end portions, the forward one of which 15 is formed with a stepped diameter and acts as a plug in the open end of the stainless steel tubular member 13. A coil winding 16 is wound on the bobbin 14 and its windings connect to the cable 2. An earth wire in the cable 2 is soldered to a spring 17 which acts as a contact with the interior of the stainless steel tubular member 13. A mild steel ferromagnetic core 18 is a free sliding fit in the bore of the bobbin 14 and is fast with a cylindrical plastics plug member 19 at its forward end. A long coil spring 20 extends from the rear plug member 7 in the annular gap between the outer and inner stainless steel tubular members 11 and 13 and holds the forward plug member 19 within its coils. The core 18 is therefore free to slide within the bore of the bobbin but is biassed forwardly gently by the coil spring 20 which provides an even restoring force over the range of travel of the core 18. The rearward end of the probe member 4 is capable of displacing the plug member 19 and core 18 rearwardly.

The probe element 3 with the cover member 6 is detachable and replaceable.

The probe member shown in FIG. 3 is a one piece plastics moulding suitably of nylon or polyester made up of the following elements integrally connected with one another end to end. At the proximal end of the probe member, there is a stiff connecting portion 22 which is a loose-fit in the plug member 19. There is then a straight portion 24 of lesser diameter, suitably about 0.5 mm which is a comfortable sliding fit within the sheath 5 and occupies a straight portion of the sheath 5 lying at its proximal end. There next follows the main portion of the probe member 4 which consists of a series of generally spherical portions 26 having a diameter of about 0.5 mm connected by bridges 28 of circular cross-section having a diameter of about 0.2 mm and a length of about 0.5 mm. As shown in FIG. 2, the portion of the probe member made up of the spherical portions 26 and bridges 28 occupies all that region of the sheath 5 which is curved.

Lastly, at its distal end, the probe member 4 has a terminal portion 30, the proximal portion of which slides within a straight terminal portion of the sheath 5 and the remainder of which protrudes from the sheath 5 to a variable extent for probing.

It is found that the tendency of the probe member 4 to take a set when stored in a curved sheath 5 is greatly reduced by the presence of the bridges 28 which are sufficiently small in diameter to be insufficiently stiff if they accept a set to have any important effect upon the sliding friction of the probe member in the sheath and at the same time are sufficiently short that they will not buckle within the sheath when the probe member experiences resistance.

The apparatus may comprise as part of a computer/printer unit a source of a driving voltage $V_1$ connected across the coil 16 via a resistor and a transistor switch. When the transistor switch is closed, current flows through the coil 16 increasing at a rate dependent upon the inductance of the coil 16. The increase in current is monitored by a pair of threshold detectors monitoring the potential drop across the resistor. When the potential monitored reaches the voltage $V_2$ set on the high threshold detector, this information is passed to the logic circuitry and causes the transistor switch to be opened. The current through the coil 16 then decays at a rate dependent upon its inductance until the potential measured at the resistor falls to the voltage $V_3$ set on the low threshold detector. When $V_3$ is reached, the information is passed to the logic circuitry which causes transistor switch to close. The transistor switch therefore closes and opens at a frequency dependent upon the inductance of the coil 16 which is dependant on the position of the core 18. From this frequency a signal representing of the coil inductance and thus the position of probe member 4 is produced.

The manner of use of the probe apparatus and the programming of the computer monitoring the probe member 4 is further explained in GB-B-2193579 and need not be further described here.

Whilst the invention has been described with reference to the illustrated embodiment, many modifications and variations thereof are possible within the scope of the invention. In particular, optionally a light conducting optical fiber may be included in the probe member 4 for use in making optical measurements in addition to distance measurements as further described in GB-B-2195379.

The larger cross-section portions of the probe member need not be spherical but may be cylindrical or of a cross-section other than circular, as may the bridges.

I claim:

1. A probe element for probe apparatus which element comprises a curved tubular sheath having a proximal end for connection to the probe apparatus and an open distal end, and a probe member within said sheath having a proximal end for connection to the probe apparatus and a distal end for protrusion from said distal end of the sheath, said sheath and probe member being slidable with respect to one another to protrude said distal end of the probe member from the distal end of the sheath by a variable amount, wherein said probe member comprises over at least a part of its length within said sheath a series of larger cross-section spheroidal portions linked by smaller cross-section flexible bridges which separate the spheroidal portions and transmit compressive and tensile forces applied to the probe member.

2. A probe element as claimed in claim 1, wherein the breadth of the larger cross-section portions in said probe member is from 0.2 to 1 mm.

3. A probe element as claimed in claim 2, wherein the breadth of said portions is about 0.5 mm.

4. A probe element as claimed in claim 1, wherein the breadth of said bridges is from 0.05 to 0.5 mm.

5. A probe element as claimed in claim 4, wherein the breadth of said bridges is about 0.2 mm.

6. A probe element as claimed in claim 1, wherein said distal end of the probe member comprises a terminal portion of substantially uniform or progressively tapering cross-section which is substantially stiffer than said part of the length of the probe member comprising said flexible bridges.

7. A probe element as claimed in claim 6, wherein at least a proximal part said terminal portion is at least substantially straight.

8. A probe element as claimed in claim 1, wherein said proximal end of said probe member comprises a relatively stiff terminal portion of enlarged breadth for connection to said probe apparatus.

9. A probe element as claimed in claim 1, wherein said larger cross-section portions of said probe member and said bridges are integrally connected.

10. Probe apparatus comprising:

a housing member, a probe element as claimed in claim 1 or and one of claims to 9, one of said probe member and said sheath being connected at its proximal end to said housing member;

slidable means disposed in said housing for sliding movement therein and coupled to the other of said probe member and said sheath to slide therewith;

and means for sensing the position of said slidable means in said housing member and for producing a signal indicative thereof and of the extent of protrusion of said distal end of said probe member from said sheath.

* * * * *